US011090437B2

(12) United States Patent
Lynch

(10) Patent No.: US 11,090,437 B2
(45) Date of Patent: Aug. 17, 2021

(54) DEVICE FOR THERAPEUTIC DELIVERY OF MEDICAL FLUID

(71) Applicant: Patrick Lynch, Camarillo, CA (US)

(72) Inventor: Patrick Lynch, Camarillo, CA (US)

( * ) Notice: Subject to any disclaimer, the term of this patent is extended or adjusted under 35 U.S.C. 154(b) by 80 days.

(21) Appl. No.: 16/124,188

(22) Filed: Sep. 6, 2018

(65) Prior Publication Data
US 2019/0070362 A1 Mar. 7, 2019

Related U.S. Application Data

(60) Provisional application No. 62/554,920, filed on Sep. 6, 2017, provisional application No. 62/554,932, filed on Sep. 6, 2017.

(51) Int. Cl.
*A61M 5/20* (2006.01)
*A61M 5/00* (2006.01)
*A61B 17/22* (2006.01)
*A61M 13/00* (2006.01)
*A61M 39/22* (2006.01)
*A61M 5/19* (2006.01)
*A61M 5/145* (2006.01)
*A61M 5/48* (2006.01)
*A61M 5/168* (2006.01)

(52) U.S. Cl.
CPC ........... *A61M 5/2053* (2013.01); *A61B 17/22* (2013.01); *A61M 5/007* (2013.01); *A61M 5/1452* (2013.01); *A61M 5/14526* (2013.01); *A61M 5/16877* (2013.01); *A61M 5/19* (2013.01); *A61M 5/484* (2013.01); *A61M 13/003* (2013.01); *A61M 39/223* (2013.01); *A61B 2017/22082* (2013.01); *A61M 2205/3344* (2013.01)

(58) Field of Classification Search
CPC ............ A61M 5/1452; A61M 5/14526; A61M 5/2053; A61M 5/484; A61M 2005/14513
See application file for complete search history.

(56) References Cited

U.S. PATENT DOCUMENTS

2005/0070848 A1* 3/2005 Kim .................... A61M 5/2053 604/140

* cited by examiner

Primary Examiner — Deanna K Hall
(74) Attorney, Agent, or Firm — Kafantaris Law Offices; Theo Kafantaris

(57) ABSTRACT

The present invention will provide a medical device that can properly regulate the working pressure of a highly pressurized gas for delivering therapeutic agents at a relatively constant flow rate during the entire course of infusion while also maintaining the integrity of the operating room and reducing risks involved with therapeutic agents. This is accomplished utilizing a pressure control assembly along with a syringe assembly or self-contained fluid chamber to administer therapeutic agents to patents in a controlled and safe manner by incorporating pressurized gas.

9 Claims, 16 Drawing Sheets

SECTION B-B

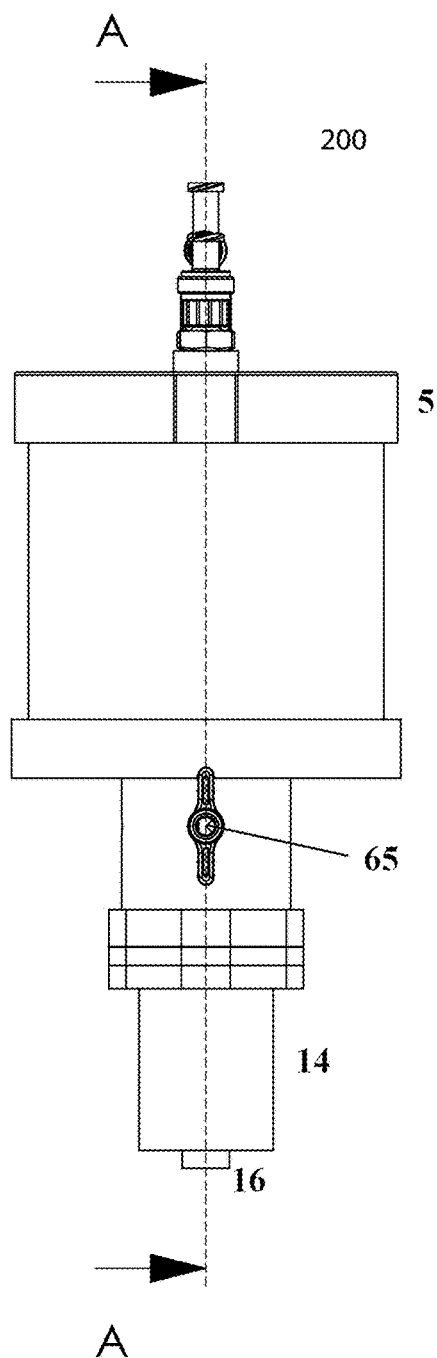
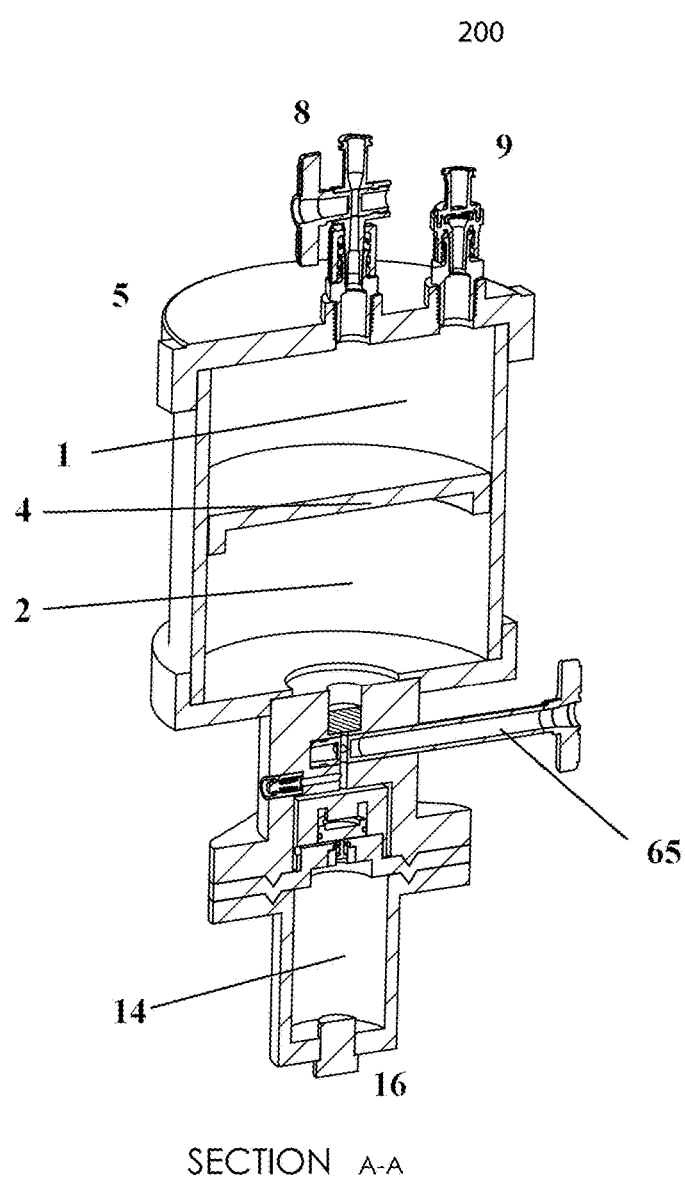
FIG. 4a
FIG. 4B

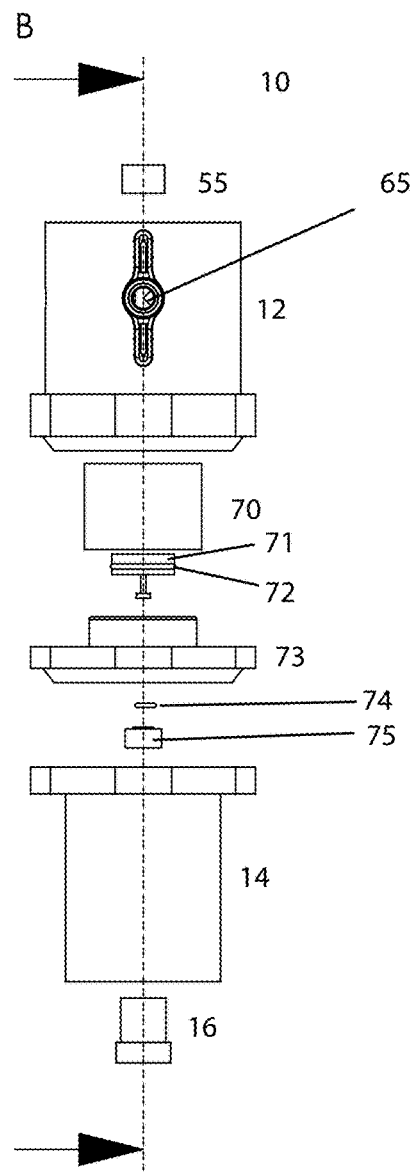
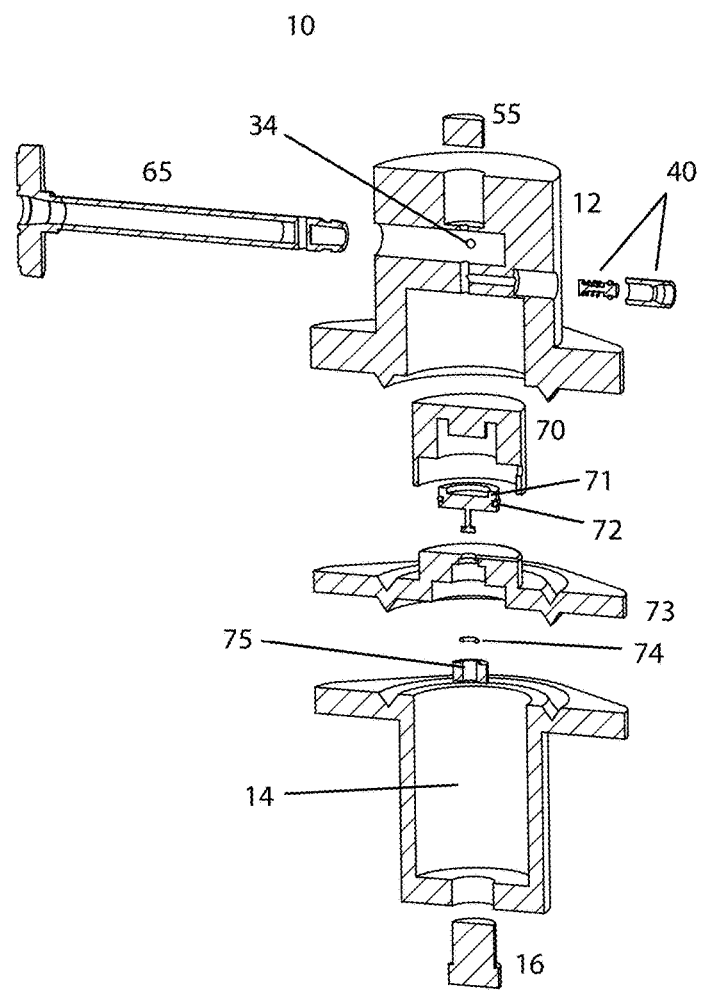
FIG. 6a
FIG. 6b
SECTION B-B

SECTION A-A

DETAIL B

DETAIL B

DEVICE FOR THERAPEUTIC DELIVERY OF MEDICAL FLUID

CROSS-REFERENCE TO RELATED APPLICATIONS

This application claims the benefit of U.S. Provisional Patent Application No. 62/554,920, filed on Sep. 6, 2017, and U.S. Provisional Patent Application No. 62/554,932, filed on Sep. 6, 2017, both of which are incorporated herein by reference.

STATEMENT REGARDING FEDERALLY SPONSORED RESEARCH AND DEVELOPMENT

Not Applicable.

FIELD OF THE INVENTION

This invention relates to a system and apparatus for delivering medical fluid and gas, and more particularly, to a system and apparatus for the controlled pressure regulated delivery of medical fluid and gases and associated embodiments of use for medical therapy.

DISCUSSION OF RELATED ART

Devices for delivering a beneficial therapeutic agent to a patient such as a drug diffused in a medical liquid are known in the art. One class of delivery devices includes disposable infusion pumps. Non-electric disposable infusion pumps have been in clinical use for more than 20 years. During these years the number of areas in which they are used has increased, as well as the number of patients receiving therapy with these devices. Today, disposable infusion pumps are extensively used in hospitals and home care settings to deliver therapies such as chemotherapy, antimicrobials, analgesia, and anesthesia, as well as for postoperative pain control and chronic pain management.

The most common disposable device utilizes an elevated glass or flexible container having a beneficial agent diffused in a medical liquid which is fed by gravity to a patient's venous system via a length of flexible plastic tubing and a catheter. The rate of flow in this type of device is commonly regulated by an adjustable clamp on the tubing. This set-up suffers from the drawback of requiring a relatively stationary patient and is dependent on the height differential between the medical liquid and the patient for accurate delivery rates. Other infusion devices have difficulty maintaining flow rate, as the variance between flow rate from the beginning to the end of fluid administration can vary greatly.

A particular problem in the art of current disposable infusion devices is achieving a relatively constant flow rate for the infusion of the liquid. This is because these devices cannot maintain a constant pressure during the entire course of the infusion. The relatively constant flow rate is particularly important when infusions over extended periods of time, such as 24 or 48 hours, are required for the drug therapy. Of particular concern is the ability to maintain a very narrow tolerance range of infusion rates volumes for highly toxic chemotherapy agents used for treating patients with cancer. While solutions of viscosity similar to water may be suitable for these devices, there are other therapeutic agents with much higher viscosities (i.e. Liquid immunoglobulin) that require a higher output pressure particularly when the agents are delivered by subcutaneous administration routes.

Medical procedures are constantly evolving to improve success rates and reduce patient risk. One such improvement involves using gas for medical purposes, where a gaseous substance is first delivered to a medical device and then delivered to the patient. Medical fields that commonly use medical gas include radiology, interventional vascular surgery, and general surgery where surgical sealants are sprayed onto the patient. $CO_2$ gas is commonly used because the human blood stream can absorb this gas type much better than other mediums, such as atmospheric air or nitrogen. However, even $CO_2$ gas can be dangerous if the working pressure is too high or large amounts are absorbed into the blood stream.

Generally speaking, medical devices involving gas will first receive a gaseous substance from a highly-pressurized source and then reduce the gas pressure to a suitable working pressure for the intended medical purpose. While this may seem like a routine task, medical environments and their inherent risks make the process much more dangerous. As an example, when using $CO_2$ gas for purposes of imaging in radiology procedures, a medical device is connected to a gas source, filled from the gas source, disconnected from the gas source, and then connected to a catheter attached to the patient, where the gas is then injected into the vascular system. If additional $CO_2$ is needed, the medical device must be disconnected from the catheter, reattached to the gas source for refilling, and then reattached to the patient as described above. Not only is this procedure tedious and time consuming, it presents a serious risk of introducing air into medical device each time it is disconnected. Injecting said air into the patient's blood vessels can be extremely dangerous and even fatal.

Furthermore, the pressurized tanks that store the medical gases are not themselves considered sterile for an operating room. In order to deliver the medical gas to the sterile side of the operating room, a transfer must occur, which breaches the operating protocol of maintaining a sterile barrier around the patient. This creates an additional risk of patient contamination resulting in potential post-operative infection. Furthermore, the logistical management of these large pressurized gas cylinders can be a safety and storage issue for an operating room. The tanks are typically too heavy for operating room personnel to transport and may not be readily available in the operating room because of their storage requirements, which could delay surgical intervention with the patient.

While medical devices which administer fluids and use gasses are becoming more and more common, there is a continued need for a medical device that can properly regulate the working pressure of a highly pressurized gas for delivering therapeutic agents while also maintaining the integrity of the operating room and reducing risks involved with therapeutic agents. The present invention satisfies these needs.

SUMMARY OF THE INVENTION

The present invention will provide a medical device that can properly regulate the working pressure of a highly pressurized gas for delivering therapeutic agents at a relatively constant flow rate during the entire course of infusion while also maintaining the integrity of the operating room and reducing risks involved with therapeutic agents. This is accomplished utilizing a pressure control assembly along with a syringe assembly or self-contained fluid chamber to administer therapeutic agents to patents in a controlled and safe manner by incorporating pressurized gas.

The present invention to provide will also provide a system for safely, reliably and conveniently delivering a regulated pressure dosage of a medical gas to a medical patient or another medical component. The present invention could be designed and manufactured for complete sterile delivery to the operating table and disposed of after use.

These and other objectives of the present invention will become obvious to those of ordinary skill in the art after reading the following detailed description of the preferred embodiments. It is to be understood that the foregoing general description and the following detailed description are exemplary, and are intended to provide further explanation of the invention as claimed.

DESCRIPTION OF THE DRAWINGS

FIG. 2a is a side view therein;

FIG. 2b is a cross-sectional view taken along line A-A of FIG. 2a;

FIG. 4a is a side view therein;

FIG. 4b is a cross-sectional view taken along line A-A of FIG. 4a;

FIG. 6a is a side exploded view of the pressure control assembly;

FIG. 6b is a cross-sectional exploded view taken along line B-B of FIG. 6a;

DETAILED DESCRIPTION OF THE PREFERRED EMBODIMENT

Figure 1A:
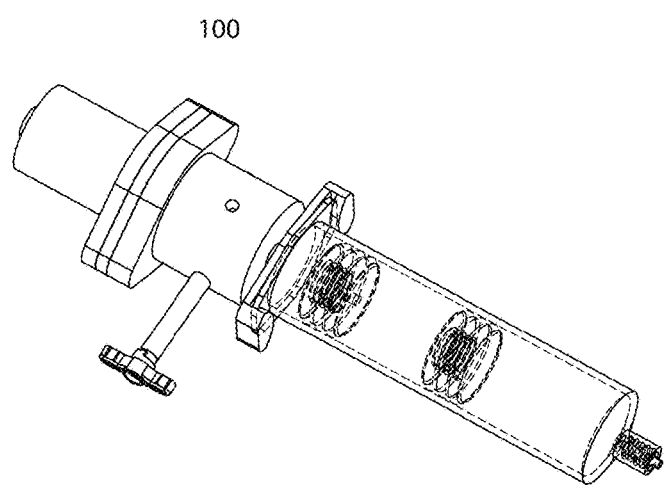
FIG. 1a is a perspective view of the syringe-based embodiment of the present invention.

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

The present invention 100 comprises a pressure control assembly 10 and various embodiments for retaining and delivering medical material. The pressure control assembly 10 comprises a high pressure chamber 14, a pressure chamber manifold 73 which seals the high-pressure chamber 14, and pressure control chamber 70 which regulates gas pressure to a working pressure chamber 12. These components work in conjunction to deliver gaseous material to a patient, medical component, or to the atmosphere by regulating a high-pressure gas to a lower, working pressure.

Figure 1B:
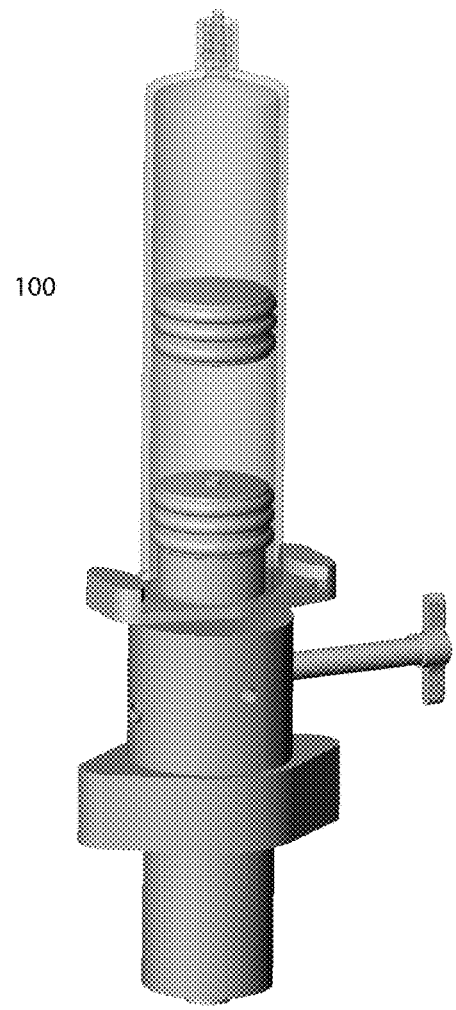
FIG. 1b is a side view therein with shading.
Figures 2A, 2B:
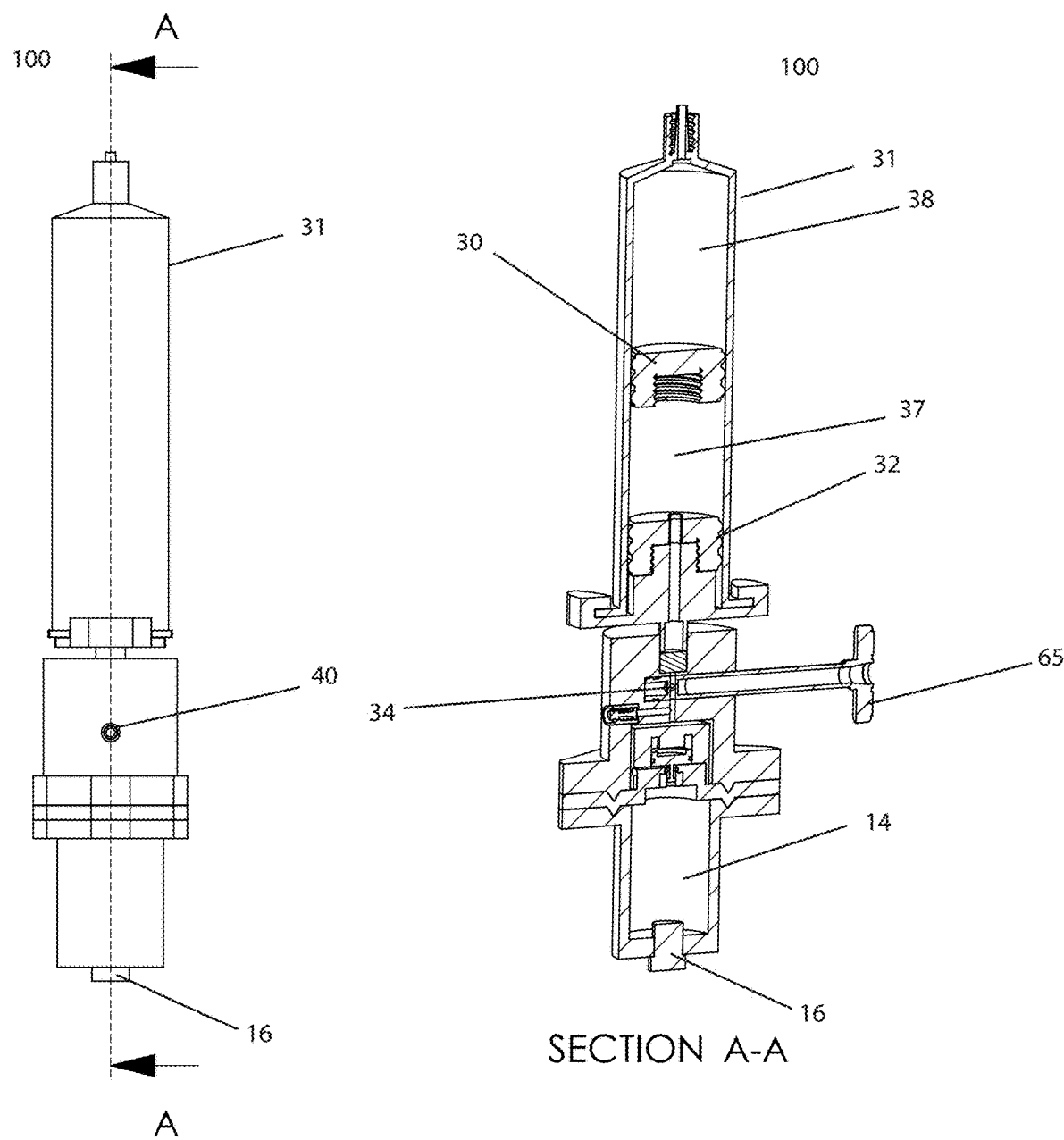
Figure 3:
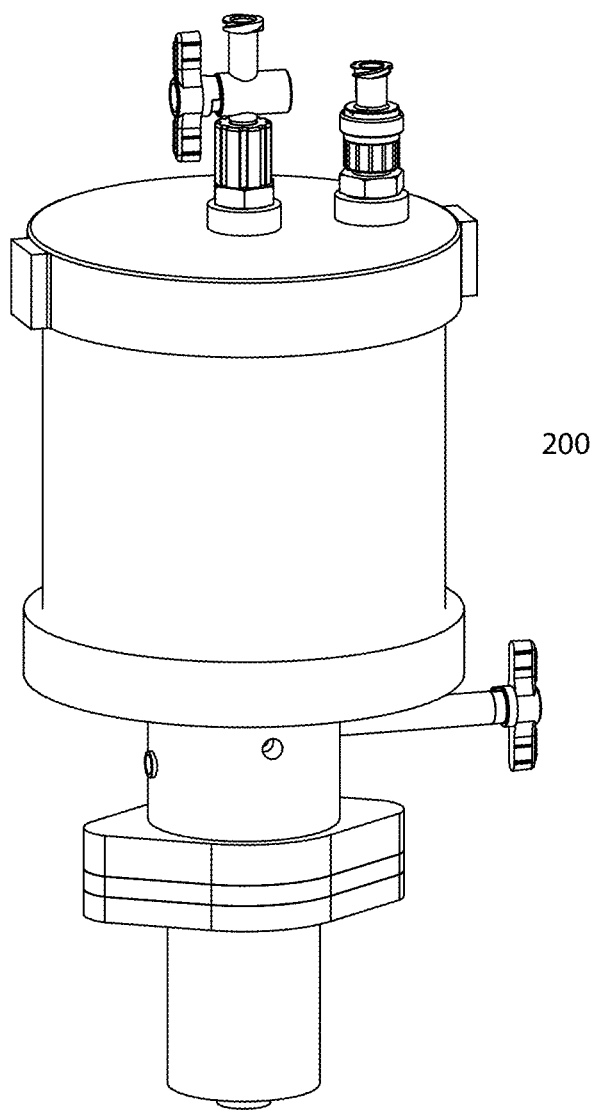
FIG. 3 is a perspective view of the self-contained embodiment of the present invention.
Figure 5:
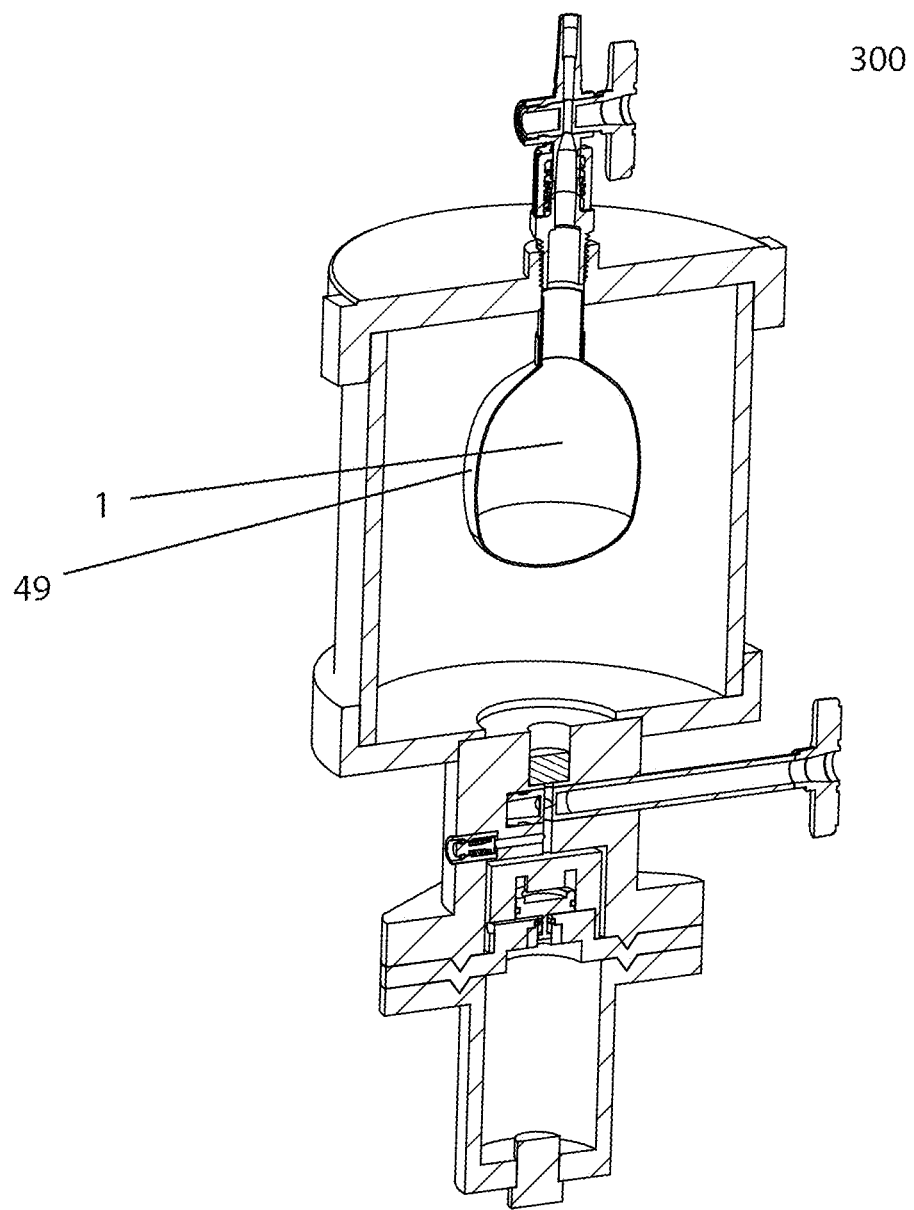
FIG. 5 is perspective cross-sectional view taken along line A-A of FIG. 4a of the self-contained embodiment of the present invention with bladder.
Figure 7A:
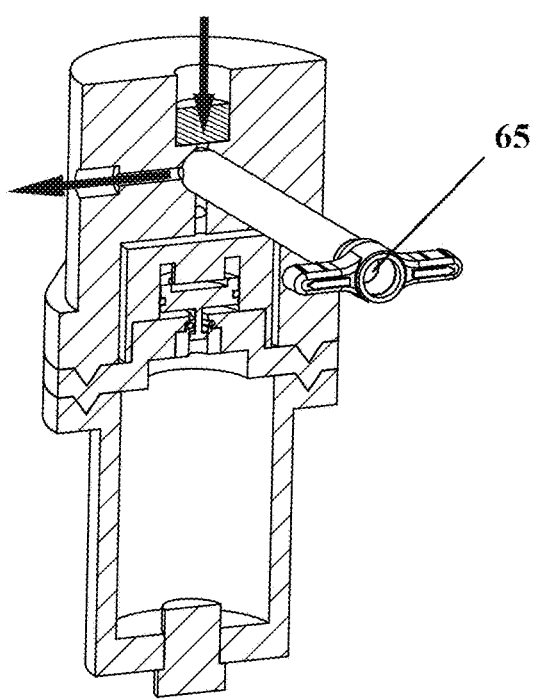
FIG. 7a is a front cross-sectional view of the pressure control assembly showing the activation valve.
Figure 7B:
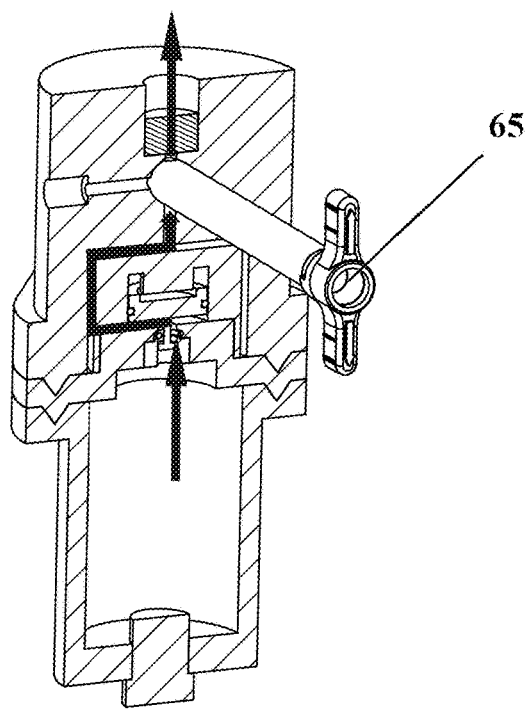
FIG. 7b is a front cross-sectional view showing the flow of gas when the activation valve is rotated 90 degrees.

In the preferred embodiment, the pressure control assembly 10 is adapted to attach directly to a syringe assembly (FIGS. 1-2) for delivering medical fluid through the syringe to a subsequent intravenous tubing set. In an alternative embodiment (FIG. 3-5), the pressure control assembly 10 is affixed to a cylinder chamber where the chamber provides an input port to receive medical fluid and an output port for delivering medical fluid. In a further alternative embodiment (FIGS. 9-14), the pressure control assembly 10 is adapted to attach to a 3-port valve assembly for delivering medical fluid for purposes of angiography or sclerotherapeutic injections of a foam-based agent.

The pressure control assembly 10 operates by displacing a piston 71 positioned within the pressure control chamber 70 which regulates the flow of gas to a working pressure in a working pressure chamber 12. The pressure control chamber 70 is mounted on top of the pressure manifold 73 and is fluidly connected to the high-pressure chamber 14. The piston 71 further comprises a piston arm that extends through the pressure manifold 73 and into the high-pressure chamber 14. The piston arm comprises a cylinder encircled with an o-ring 72 positioned inside the pressure control chamber 70 to provide a pressure-tight seal between the piston 71 and the pressure control chamber 70. The high pressure within the high-pressure chamber 14 displaces the piston 71 into the pressure control chamber 70 until the arm of the piston 71 makes contact with a sealing o-ring 74 positioned within the pressure manifold 73 which terminates the fluid connection to the working pressure chamber 12. The sealing o-ring 74 is secured in place in the pressure manifold 73 with an o-ring retainer component 75. Based upon the internal volume of the pressure control chamber 70, the displacement of the piston 71 compresses the gas within the pressure control chamber 70 to the desired working pressure of the apparatus, also referred to as the reference pressure.

When the pressure in the working pressure chamber 12 is reduced below the reference pressure, the exceeding positive pressure of the pressure control chamber 70 will displace the piston component 71 back into the high-pressure chamber 14 allowing more high-pressure gas to flow between the piston arm and the sealing o-ring 74 and into the working pressure chamber 12. This will subsequently create a rise in pressure in the working pressure chamber 12 which will displace the piston component 71 into the pressure control chamber 70 until the reference pressure is achieved and the piston arm terminates fluid connection by making contact with the sealing o-ring 74. Various methods can be used to attach the high-pressure chamber 14, pressure manifold 73, and working pressure chamber 12 together. The method depicted in the drawings utilizes tongue and groove features to support ultrasonic welding assembly. The method depicted in the drawings to secure the pressure control chamber 70 to the pressure manifold 73 is an interference fit assembled with compression or press equipment.

The piston 71 dynamically moves back and forth between the high-pressure chamber 14 and the pressure control chamber 70 based upon the current pressure within the working pressure chamber 12. As the user demands regulated gas flow, a pressure drop is created in the working pressure chamber 12 and when gas pressure in the working pressure chamber 12 drops below the reference pressure, gas volume is replaced from the high-pressure chamber 14 to restore equilibrium. The volume and charging pressure of the high-pressure chamber 14 is determined based upon the intended use of the pressure control apparatus 10 to deliver a sufficient volume of medical gas at the desired regulated pressure.

In the preferred embodiment, the high-pressure chamber 14 is filled with pressurized gas through the proximal end of the high-pressure chamber 14 and then sealed closed with a gas fill port 16. The initial charging pressure of the high-pressure chamber 14 will be established to provide sufficient volume of pressurized gas to maintain a constant working pressure within the working pressure chamber 12 for the entire range of therapeutic liquid volume or therapeutic gas volume required for the intended procedure. Rubber plug piston gasser equipment is used in the aerosol industry to support this method of gas charging and sealing in a container.

An activation valve 65 is positioned within the working pressure chamber 12 to fluidly connect or terminate the regulated gas flow from the working pressure chamber 12 to atmosphere, a patient, or other medical component. The activation valve 65 comprises three throughs hole positioned to allow either fluid connection from the gas pathway between the high-pressure chamber 14 to the working pressure chamber 12 or if the activation valve is rotated, it provides a gas pathway from the working pressure chamber 12 to atmosphere via a vent pathway 34. The activation valve 65 can be rotated 90 degrees to either align the through hole in the activation valve shaft 65 with the fluid path of the working pressure chamber 12 or terminate the fluid connection and allow venting of the working pressure chamber 12 to atmosphere via vent pathway 34.

The working pressure chamber 12 further comprises a pressure relief valve 40 for safety precautions, where the limit of the pressure relief valve 40 is set at a limit above but close to the desired reference pressure. The pressure relief valve 40 prevents excess pressure from being released from the working pressure chamber 12, which is imperative for medical use where the administered gaseous fluid may be in direct contact with a patient. In the event of a pressure regulation failure caused by sources such as defective components, the pressure relief valve 40 provides additional safety assurances and will vent the excessive pressure to atmosphere. In the preferred embodiment, the pressure relief valve comprises a spring-based actuation mechanism. The pressure relief valve 40 can be affixed to the working pressure chamber 12 through interference press fit or threaded insertion.

The syringe-based embodiment 100 of the present invention (FIGS. 1-2) will incorporate the pressure control assembly 10 to regulate high-pressure gas as a means of delivering medical fluid, where three primary individual chambers exist. The first and second chambers 38, 37 are provided by the use of a syringe 31 with a detachable plunger component 29 from the piston component 30 of the syringe assembly, while the third chamber is the high-pressure chamber 14 of the pressure control assembly 10. Here, a syringe 31 is used to withdraw the therapeutic agent from its storage component. The syringe 31 will include a syringe piston 30 that is attached to a syringe plunger 29 by threaded connection or other connection methods facilitating simple removal of the syringe plunger 29 from the syringe piston 30 while the syringe piston 30 is left still positioned inside the syringe barrel 31.

For the syringe-based embodiment, the syringe 31 is first filled with therapeutic agent by pulling back on the piston 30 and plunger 29 components. Once filled to a desired volume, the plunger 29 is detached from the piston 30 and removed from the body of the syringe 31. The pressure control assembly 10 is then inserted into the proximal end of the syringe barrel 31. The insertion of piston 32 into the syringe will cause the pressure to increase because of the volume compression it will create in the second chamber 37 which is then vented through the 3-way pressure relief valve 65 and relief orifice 34 fluidly connecting the second chamber 37 to atmosphere. If this pressure was not vented, then the piston 30 within the syringe would either be displaced forward, or the second chamber would be over-pressurized and result in either premature ejection of therapeutic agent or reside at a higher than desired initial working pressure which can affect the resulting flow rate of the therapeutic liquid from the syringe.

Figure 16:
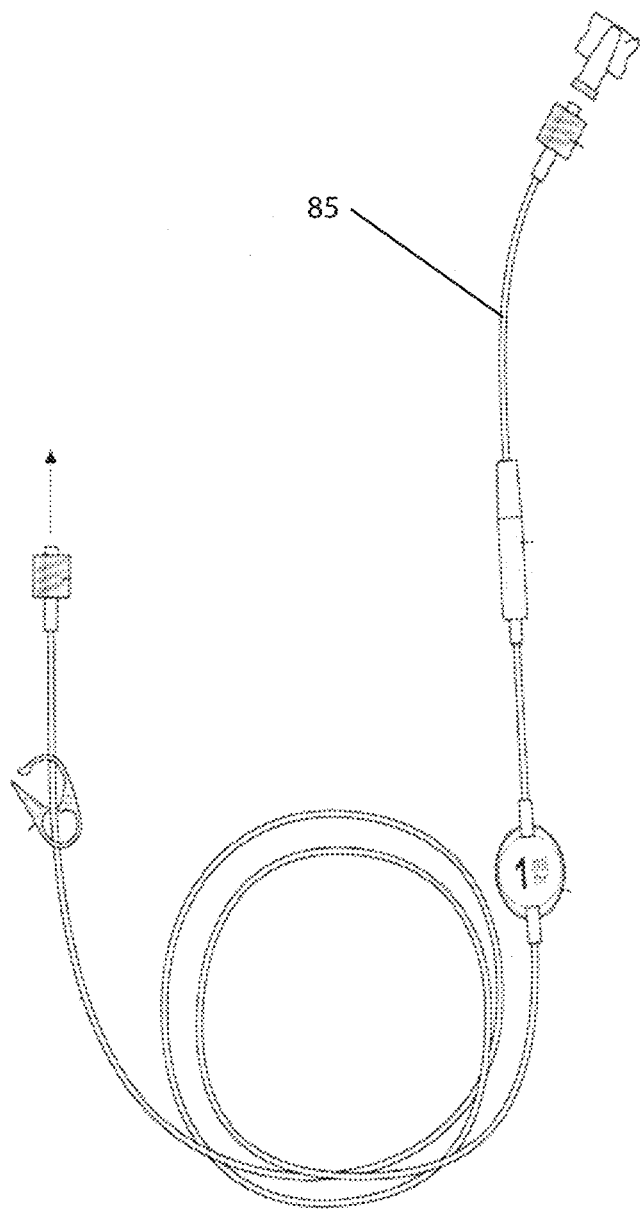
FIG. 16 illustrates an intravenous tubing set for infusion pumps.

For the syringe-based embodiment, a valve or clamp located in a common infusion tubing set in a distal position to the syringe will be opened to initiate flow of therapeutic agent (See FIG. 16). As the liquid is displaced from the first chamber 38 of the syringe, the volume in the second chamber 37 of the syringe will increase and subsequently the pressure within the second chamber 37 will drop. In order to maintain a constant flow rate of the therapeutic agent over the entire volume of liquid therapeutic agent, the working pressure in the second chamber 37 should be as constant as possible.

In the self-contained embodiments (FIGS. 3-5) 200, the first chamber 1 is designated to receive the therapeutic liquid which is filled at time of use. The user who is filling the device will commonly use a standard syringe or pump to fill the therapeutic liquid through the fill valve 9 of the self-contained embodiment. Dividing the first chamber 1 from the second chamber 2 is a displaceable piston member 4. This piston member 4 is gas and liquid sealed between the first and second chamber 1, 2. The second chamber 2 is also referred to as the working pressure chamber. Its function is to displace the therapeutic liquid agent in the first chamber 1 through the exit valve 8. The exit valve 8 is positioned on the top container cap 5 of the self-contained embodiment 200. With the device in the unfilled state, the piston member 4 is positioned at the top of the first chamber 1. As therapeutic liquid is filled into the first chamber 1, the piston member 4 will displace in the direction of the second chamber 2.

To deliver the therapeutic liquid agent to the patient in the self-contained embodiment 200, the exit valve 8 on the top container cap 5 is opened. Alternatively, an exit valve 8 could be created where the top container cap 5 includes a vial stopper to sterilely seal the first chamber 1 that is pre-filled at the manufacturer site with therapeutic fluid, and then at time of use, the vial stopper is punctured with a needle-based tubing set that would contain a valve or flow stopping component to serve as the exit valve 8. The positive pressure in the second chamber 2 will displace the piston member 4 in the direction of the first chamber 1 and subsequently displace the therapeutic liquid agent from the first chamber 1 out of the exit valve 8. As the liquid is displaced from the first chamber 1, the volume in the second chamber 2 will increase and subsequently the pressure within the second chamber 2 will drop. In order to maintain a constant flow rate of the therapeutic agent over the entire volume of liquid therapeutic agent, the working pressure in the second chamber 2 should be as constant as possible.

In a bladder embodiment 300 derived from the self-contained embodiment 200, the first chamber 1 resides inside a compressible sealed bag or bladder 49 such as an aerosol bag-on-valve component, and the lining of this bag or bladder 49 serves as the piston component where the bag or bladder 49 is compressed by the pressure in the second chamber 2 and subsequently displaces the fluid in the first chamber 1 out of the exit valve 8. The first chamber 1 can be filled through the exit valve 8. Additionally, as the first chamber 1 is filled, the bag or bladder 49 will expand resulting in an increase in pressure because of volume compression in second chamber 2, where increased pressure can be vented through the vent valve apparatus previously described herein.

The three-port valve assembly embodiment (FIGS. 9-14) will deliver medical gas for purposes of angiography or sclerotherapeutic injections of a foam-based agent. Here, the pressure control assembly 10 will be fluidly connected to a 3-way valve 20, a syringe and piston with plunger assembly 29 31 that is fluidly connected to the 3-way valve 20, and gas delivery line that is fluidly connected to the 3-way valve 20. At time of design and manufacturing, the reference pressure of the pressure control apparatus 10 is established to provide the desired working pressure of the syringe assembly 29 31. For angiography purposes, a reduced pressure of 2-5 psi into the syringe chamber would be appropriate. The gas delivery line can contain a pressure relief valve 40 to provide final depressurization of the line prior to patient vascular administration. The other main component in the gas delivery line is a manual push button valve 50 that creates a final fluid connection of the gas to the patient that can be actuated conveniently by the user.

Alternatively, where it is desired to mix a medical gas source with a material contained in a primary container, the gas delivery line can be replaced with a docking port to accept a primary container such as a syringe containing a medical component. When the 3-way valve 20 is positioned to create a fluid connection between primary container with plunger assembly 29 31, the medical gas can be transferred to the primary container containing a medical component. Where uniform mixing is desired between the medical gas and the medical component, fluid transfers can be conducted back and forth between the syringe and piston with plunger assembly 30 31 32 and the primary container in a manner like the established Tessari method for creating foam mixtures of medical gas with sclerotherapeutic agents.

As gas is filled into the syringe body 30, the plunger 29 will be displaced and the pressure in the syringe will drop. As the pre-determined working pressure of the syringe 30 drops below the reference pressure during gas filling, the piston component 71 within the pressure control apparatus 10 will open and create a fluid pathway between the high-pressure chamber 14 to the second chamber 12. The valve component 65 will be positioned to allow fluid pathway of gas to the 3-way valve 20 and ultimately to the syringe assembly if the 3-way valve handle 21 is positioned in the orientation providing a fluid connection between the pressure control apparatus 10 and the syringe 30.

Figure 8A:
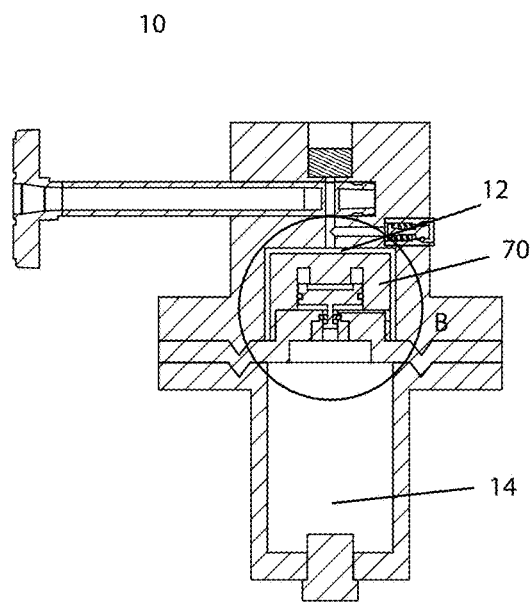
FIG. 8a is a side view taken along line A-A of FIG. 4a showing the pressure control assembly.
Figure 8B:
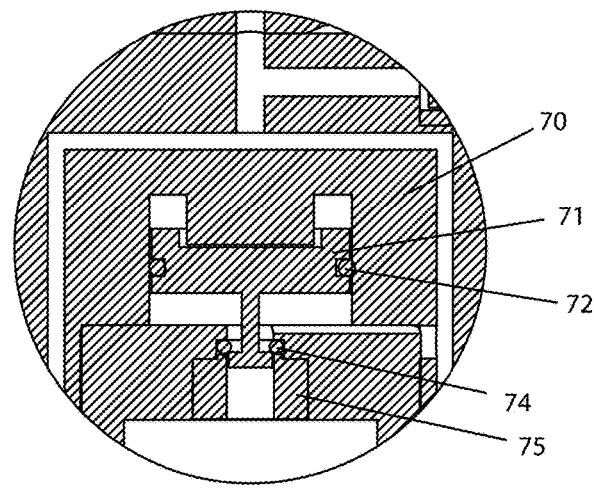
FIG. 8b is detail view of circle B of FIG. 8a in a closed position.
Figure 8C:
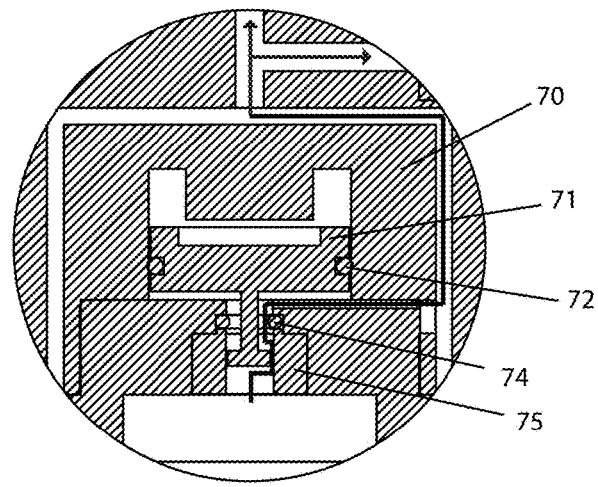
FIG. 8c is detail view of circle B of FIG. 8a in an open position.
Figure 9:
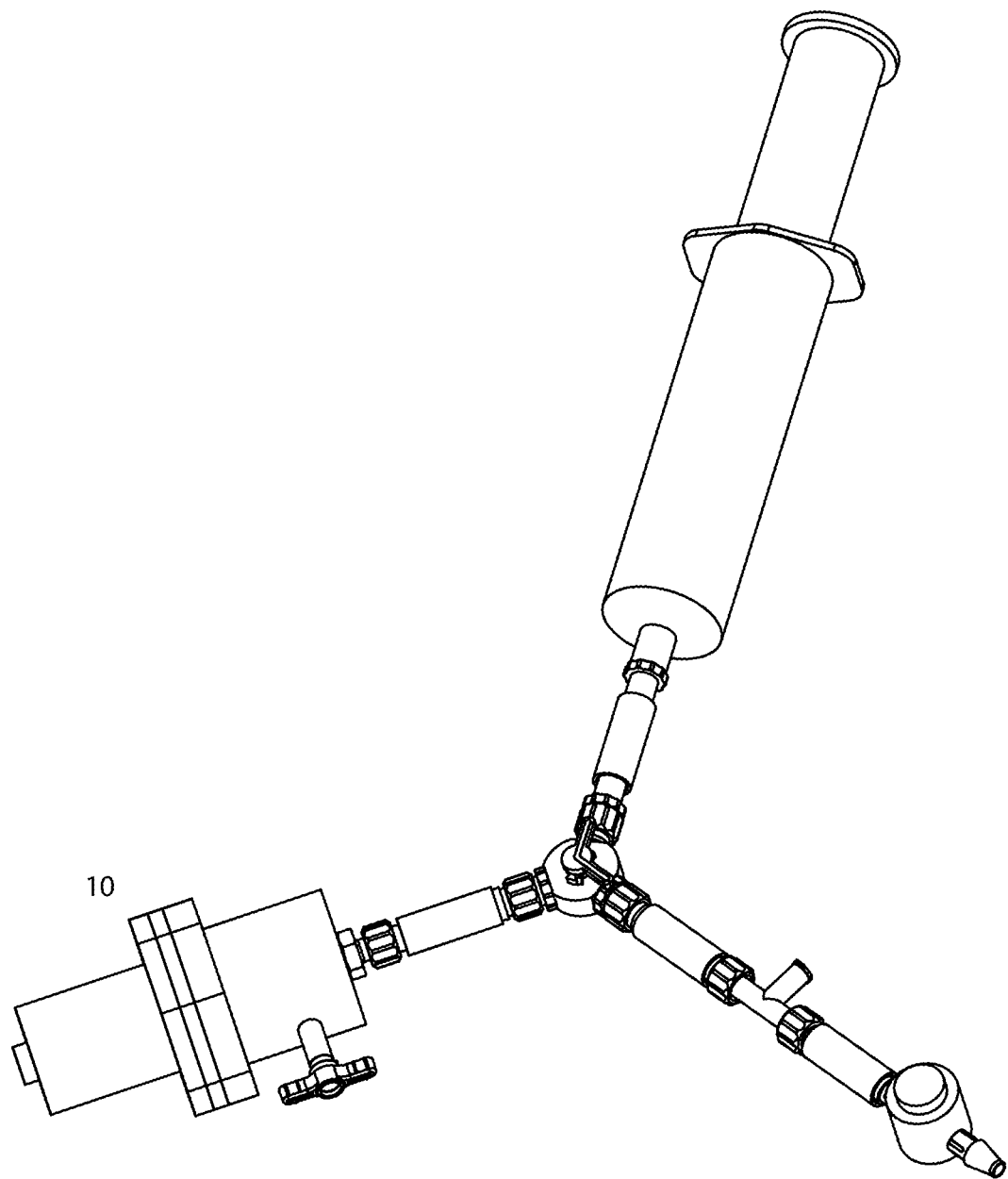
FIG. 9 is a perspective view of the three-port valve assembly embodiment of the present invention.
Figure 10:
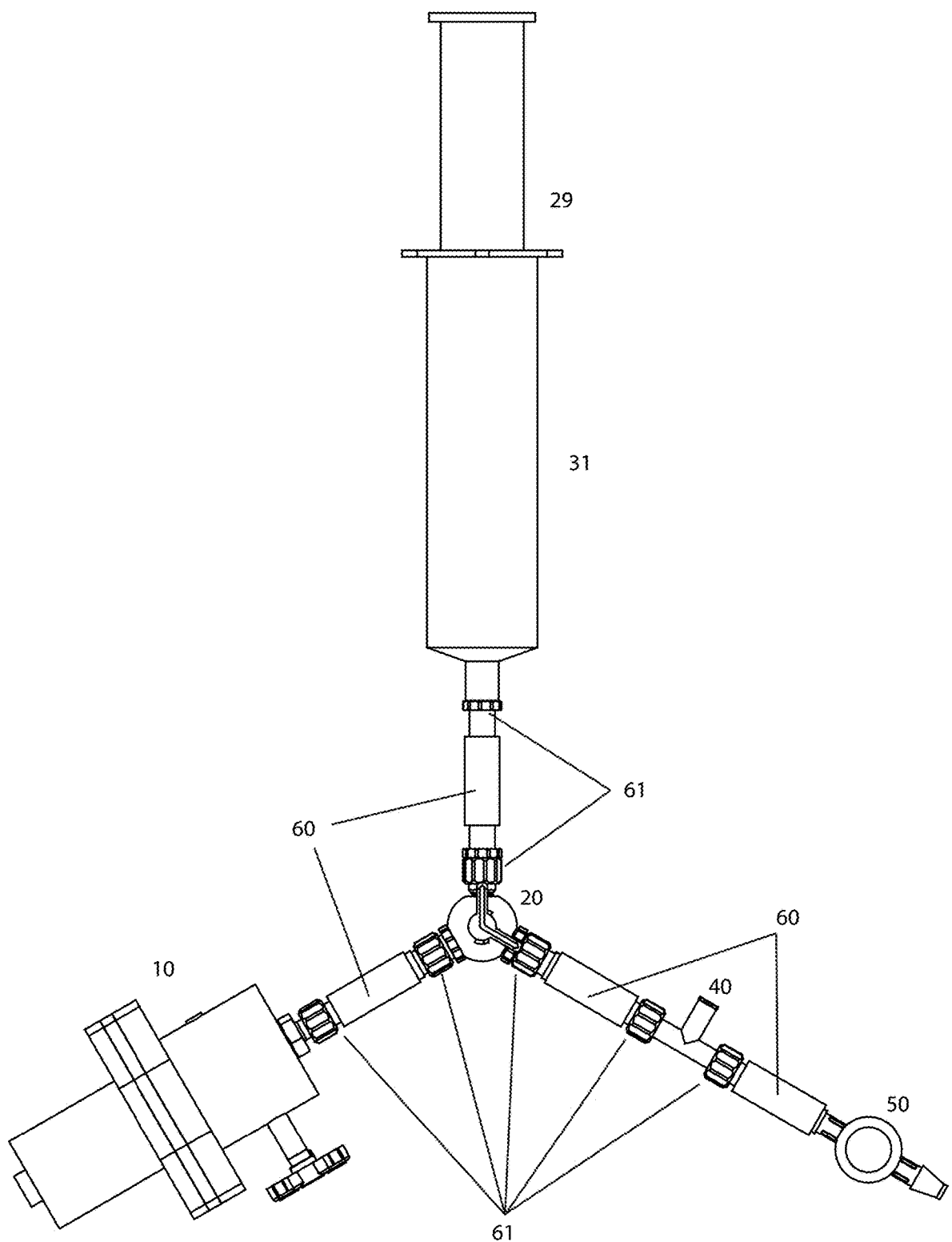
FIG. 10 is a front view therein.
Figure 11:
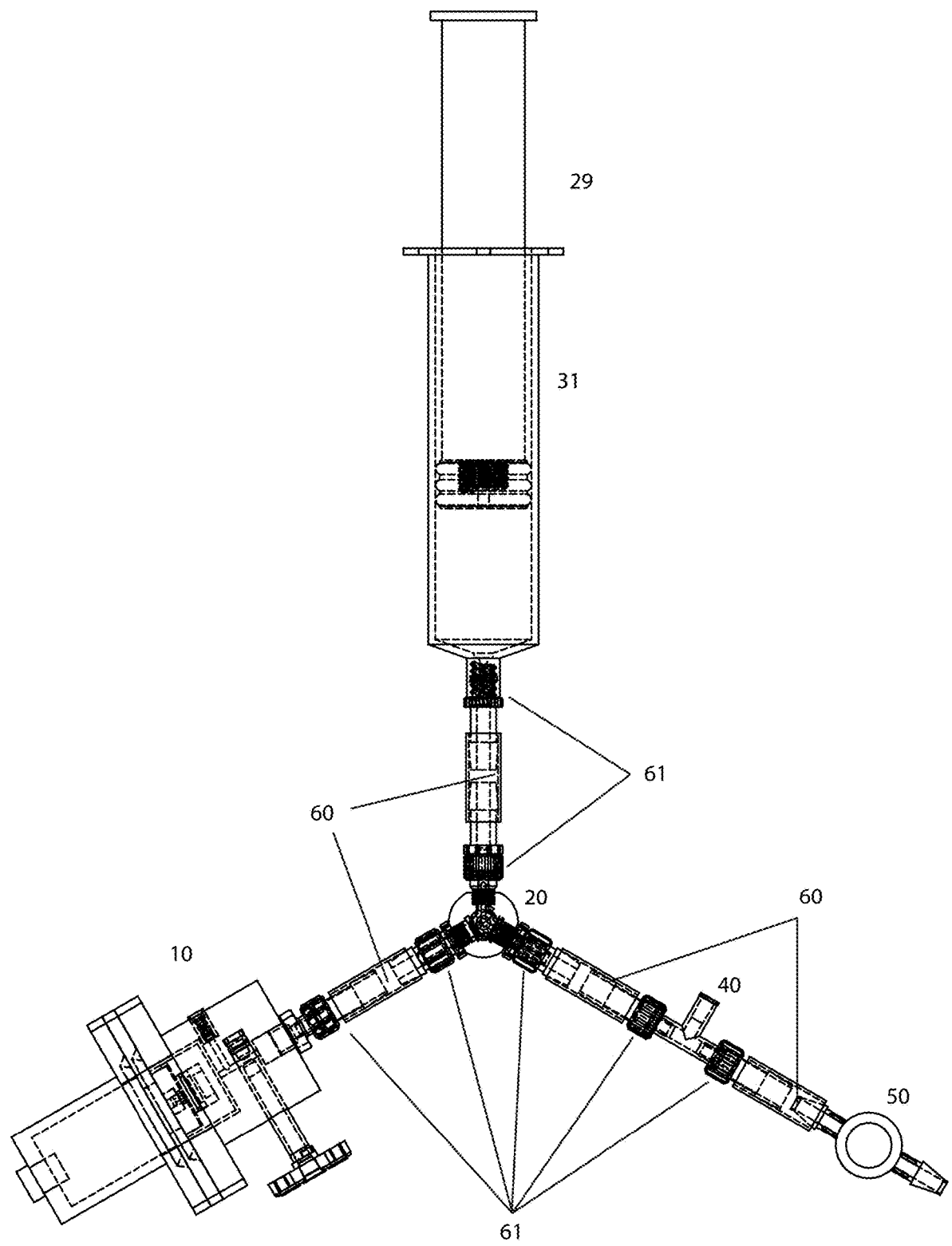
FIG. 11 is a front view therein showing hidden lines.
Figure 12A:
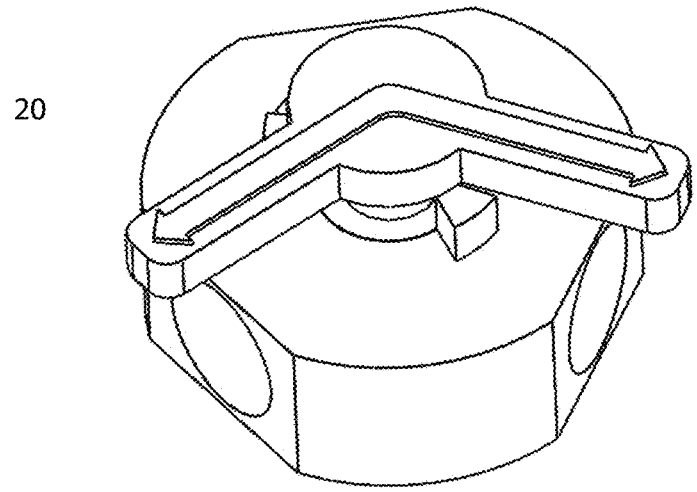
FIG. 12a is a perspective view of the 3-way valve with ports at 120-degree positions.
Figure 12B:
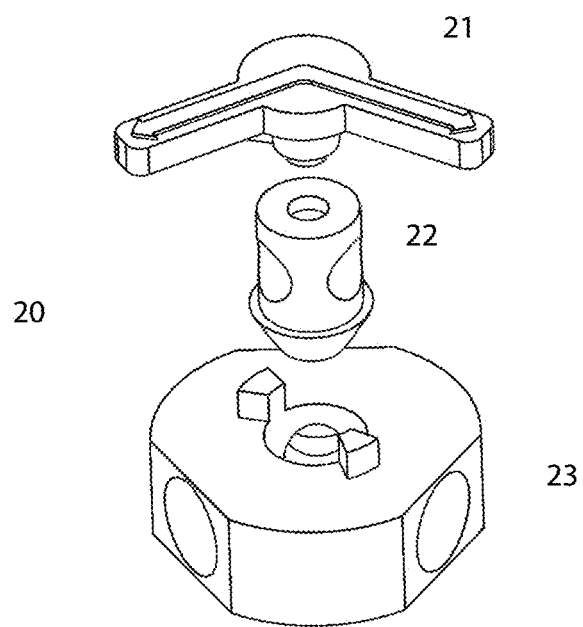
FIG. 12b is an exploded view therein.
Figure 13A:
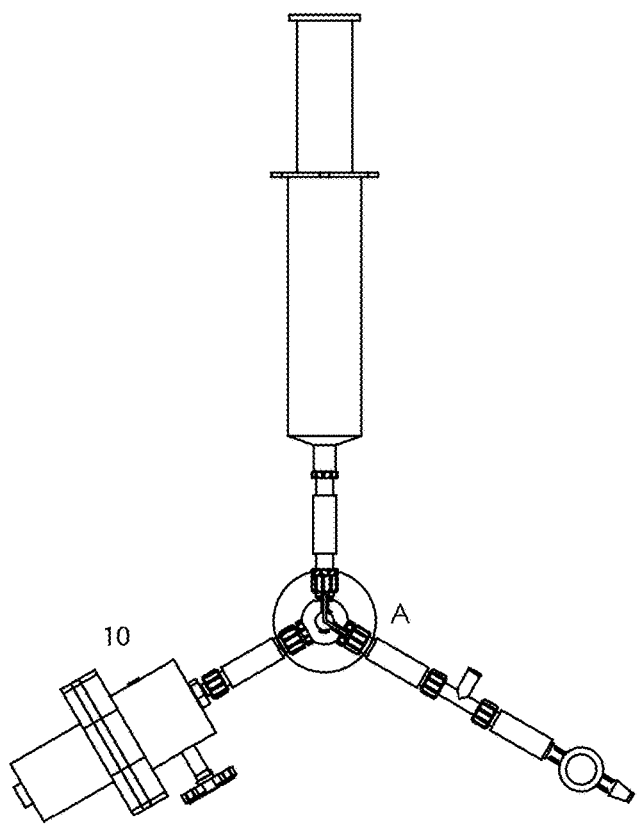
FIG. 13a is a front view of the three-port valve assembly embodiment in position for flow from the syringe to the gas delivery line.
Figure 13B:
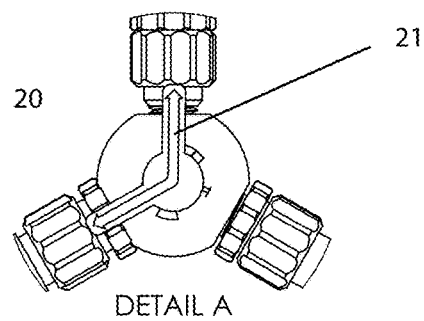
FIG. 13b is a front detail view of the three-port valve assembly embodiment in position for flow from the pressure control apparatus to the syringe.
Figure 13C:
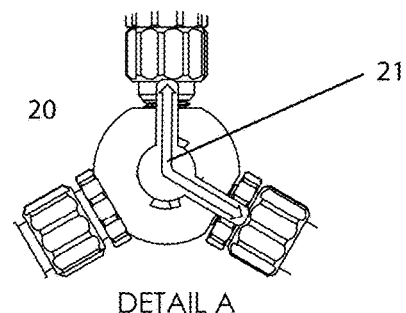
FIG. 13c is a front detail view of the three-port valve assembly embodiment in position for flow from the syringe assembly to gas delivery line.
Figure 14:
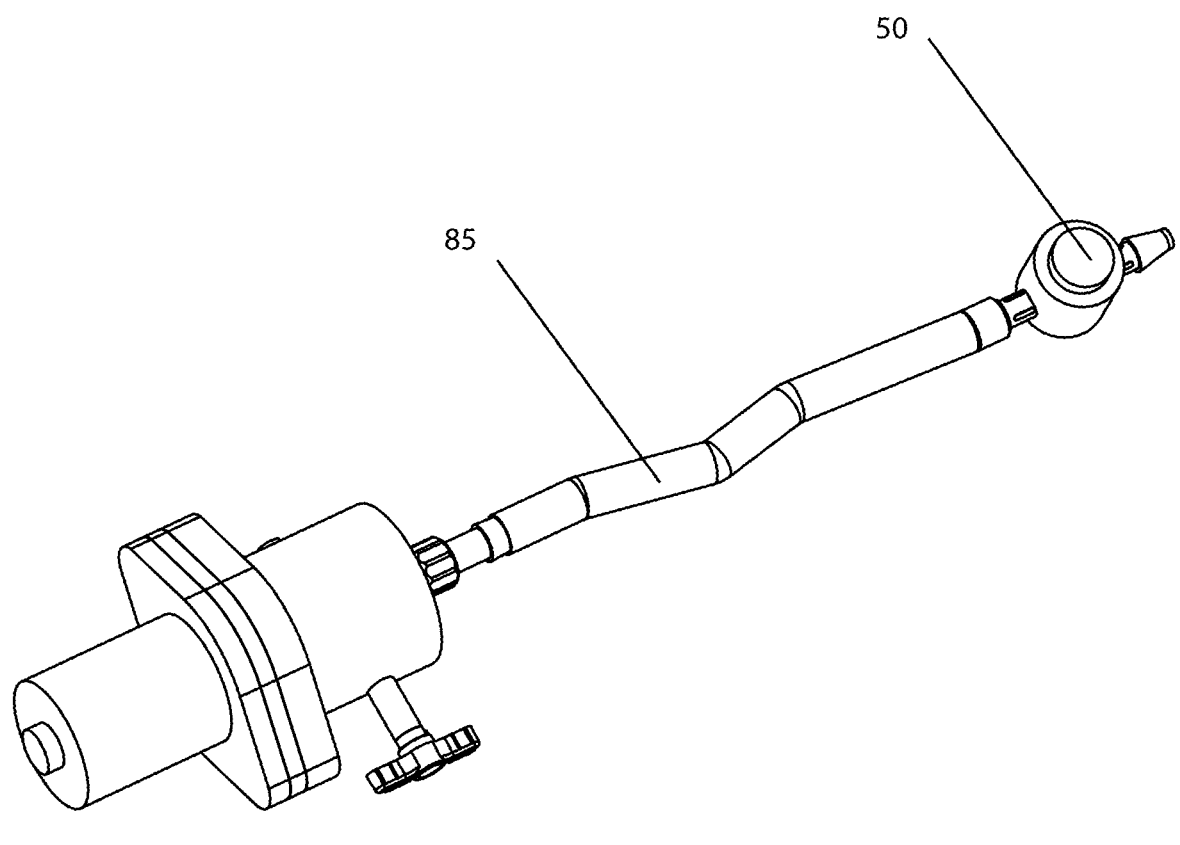
FIG. 14 is perspective view of the pressure control apparatus connected to a tubing set with a manual push button valve positioned within the fluid path of the tubing set which controls the flow of gas exiting the tubing set.
Figure 15A:
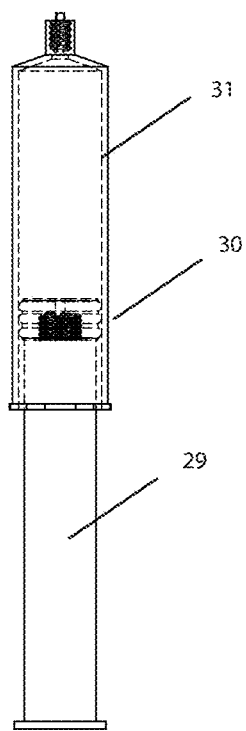
FIG. 15a is a front view of a standard therapeutic syringe with a plunger and piston positioned inside a filled syringe.
Figure 15B:
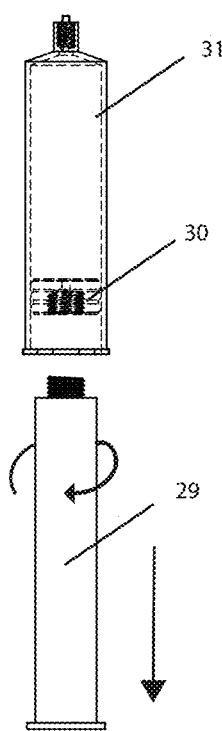
FIG. 15b is a front view of a standard therapeutic syringe with the plunger unscrewed from the piston and removed from the syringe.
Figure 15C:
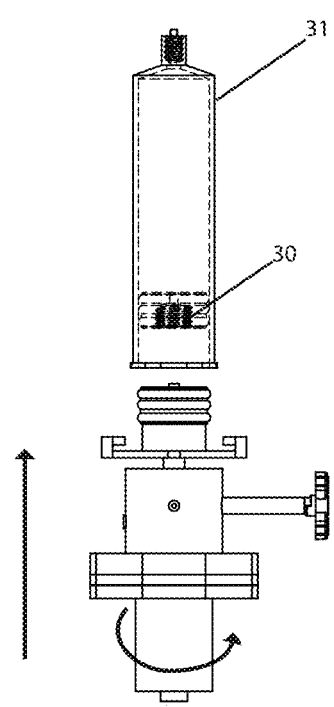
FIG. 15c is a front view of a standard therapeutic syringe with a displaceable piston and the pressure control assembly of the invention prepared for insertion into the barrel of the syringe.

The high-pressure chamber 14 is intended to contain a higher pressure gas than the working pressure which is within the syringe 30 and with sufficient volume for syringe displacement or even excessive volume to allow sequential syringe recharges with pressurized gas. The amount of total gas volume available can vary depending upon the specific use objective of the overall apparatus. When the valve component 65 is opened, the gas flow will travel from the second chamber 12 to the syringe 30 by pathway of the 3-way valve 20. This will result in an increase in the syringe's pressure. Once the pressure in the syringe 30 reaches the reference pressure which is in fluid connection with the second chamber 12, the valve 71 within the pressure control apparatus 10 will close (See FIG. 8b for illustration of closed position) and terminate the fluid connection between the high-pressure chamber 14 and the second chamber 12. The pressure regulation between the high-pressure chamber 14 and the syringe 30 will dynamically occur throughout the entire gas filling process of the syringe 30.

The working pressure delivered to the syringe, as defined by the reference pressure in the pressure control apparatus 10, is defined by the application need. For an angiography contrast apparatus, it may be desired to provide a working pressure to the syringe that is sufficient to displace the syringe plunger 31 without the need of a user's manipulation on the plunger of the syringe. Depending upon the size of the syringe and the force resistance between the plunger and the syringe, a different working pressure may be required to displace the plunger.

Once the syringe has been displaced with the desired volume of gas from the pressure control apparatus 10, the 3-way valve handle 21 will be rotated to terminate the fluid pathway between the pressure control apparatus 10 and the syringe 30. The handle 21 will then be rotated to achieve a fluid connection between the syringe 30 and the gas delivery line. A pressure relief valve 40 resides in the gas delivery line. This component's function is to reduce any excessive pressure from the gas delivery line to the desired pressure intended for delivery to the patient. The pressure relief valve 40 can be constructed of a 3-way tee with one port dedicated to housing the pressure relief valve 41.

A pressure relief valve 40 may be essential if the working pressure in the syringe was established at a level high enough to displace the syringe plunger without the need of the user's hands to manually retract the plunger, but where this working pressure may be too high and thus unsafe to directly introduce into a patient's vascular system. Thus, the pressure relief valve 40 can reduce the final pressure delivered to the patient to a safe level.

The final component in the gas delivery line is the manual push button valve 50. This valve prevents the flow of gas to the patient, until the valve is manually activated by the user. The valve does not have to be exclusively a push button valve, and could be any valve that a user can interact with to terminate a fluid connection in a pressure line (ie. Stopcock valve, electronically activated solenoid valve). The use of a manual push button is simply a very convenient and inexpensive method to open and close the gas flow path with minimal user interaction.

The 3-way valve 20 provides the fluid connections between the pressure control apparatus 10 to the syringe 30 and from the syringe 30 to the gas delivery line. While other valves could be used in this apparatus such as a common 4-way stopcock, these other alternatives do not provide as safe a method as that proposed with the 3-way valve 20. The inadequacy of these other valves is that they have multiple available combinations of fluid connections, with one possible connection resulting in a direct fluid connection between the pressure control apparatus 10 to the gas delivery line. While there are some safeguard components in the gas delivery line, a direct fluid connection between the pressure control apparatus 10 to the gas delivery line could result in significant patient injury or death if any component were to malfunction. Therefore, to maximize safety, preventing the possibility of this fluid connection between the pressure control apparatus 10 and the gas delivery line is critical. The 3-way valve 20 accomplishes this. The 3-way valve 20 consists of three components. The handle 21, diverter 22, and manifold 23. The manifold 23 consists of three fluid ports that are oriented 120-degrees from each other in the same plane. The diverter 22 is inserted into the manifold 23 and possesses two fluid connection ports that are oriented 120 degrees from each other in the same plane. The orientation of the ports in both the diverter 22 and the manifold 23 ensure that only two pathways of fluid connection can be created with this assembly. Features positioned on the manifold 23 prevent the handle 21 from 360-degree rotation so the handle 21 can only move between two fluid connection states, which are pressure control apparatus 10 to syringe 30, and syringe 30 to gas delivery line. Visual guidance arrows are represented on the handle 21 to inform the user of which fluid connection state the apparatus currently resides.

During manufacturing, the handle 21 is oriented to the fluid connection between the syringe 30 and the gas delivery line. This terminates the fluid connection between the pressure control apparatus 10 to the syringe 30. Once the user is ready to use the apparatus, the user would then rotate the handle 21 to the orientation to connect the pressure control apparatus 10 to the syringe 30. The user would then rotate the valve component 65 on the pressure control apparatus 10 to provide a fluid path of gas flow from the pressure control apparatus 10 to the 3-way valve 20.

The main components of the embodiment can be fluidly connected to each other using a variety of common components for fluid path construction. These components can consist of but not limited to components such as plastic tubing 60, luer connectors with barbed tubing ends and luer connectors with threaded ends 61.

Another embodiment of the present invention (FIG. 14) is use of the pressure control apparatus 10 to provide a pressure regulated flow of gas for applications such as the aerosolized spraying of biomaterials for medical procedures. In this embodiment, the pressure control apparatus 10 is connected to a tubing set 85 that also contains a flow control switch such as a manual push button valve 50. The tubing set can be attached to a spray device that is affixed to the biomaterial containers such as syringes to provide a pressure regulated flow of gas to the spray device to assist in the application of the biomaterials with an aerosolized application.

The present invention 10 is adapted to deliver pressure-regulated medical gas directly to a patient in some embodiments, although medical gas is known to still contain impurities and contaminants. As such, the working pressure chamber further comprises a sterile filtration membrane 55 for purifying the medical gas before distribution. The sterile filtration membrane comprises hydrophobic and oleophobic polyethersulfone membranes and other materials can provide effective filtration and sterilization of medical gases. For the pressure control apparatus 10, the sterile filtration membrane 55 is die cut and placed in the fluid path of the working pressure chamber 12.

While the above description contains specific details regarding certain elements, sizes, and other teachings, it is understood that embodiments of the invention or any combination of them may be practiced without these specific details. Specifically, although colors are designated in the above embodiments, any color may be used. These details should not be construed as limitations on the scope of any embodiment, but merely as exemplifications of the presently preferred embodiments. In other instances, well known structures, elements, and techniques have not been shown to clearly explain the details of the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A therapeutic liquid dispensing device comprising:
a therapeutic fluid chamber adapted to dispense liquid;
a working pressure chamber adapted to provide a working pressure at or below a reference pressure, said working pressure chamber mechanically connected to said therapeutic fluid chamber;
a high-pressure chamber adapted to provide pressurized gas from the high-pressure chamber to the working pressure chamber; and
a pressure control assembly positioned between said high-pressure chamber and said working pressure chamber, said pressure control assembly further comprising a pressure control chamber and a piston positioned inside said pressure control chamber, said piston adapted to dynamically provide or terminate a fluid connection between said high-pressure chamber and said working pressure chamber based upon the pressure differential between said pressure control chamber and said working pressure chamber;
wherein said piston and said pressure control chamber regulate the pressure of gas from said high-pressure chamber into said working pressure chamber and provide a constant working pressure inside the working pressure chamber to a reference pressure for the entire duration of liquid dispensation.

2. The device of claim 1, further comprising an activation valve in fluid connection between the high-pressure chamber and working pressure chamber, said activation valve adapted to actuate the pressurized gas from the high-pressure chamber to the working pressure chamber at time of liquid dispensation.

3. The device of claim 2, wherein said activation valve further comprises fluidly connecting the working chamber to atmosphere and fluidly disconnecting the high-pressure chamber from the working pressure chamber for purposes of venting the accumulated pressure within the working pressure chamber during filling of therapeutic fluid chamber or terminating positive pressure to the working chamber.

4. The device of claim 1, further comprising a pressure relief valve in fluid connection with the working pressure chamber, said pressure relief valve adapted to release gas pressure above the reference pressure to prevent over pressurization in the event of component failure.

5. The device of claim 1, further comprising a displaceable piston positioned between said therapeutic fluid chamber and said working pressure chamber, said working pressure chamber mechanically connected to said therapeutic fluid chamber through said displaceable piston, said displaceable piston adapted to provide pressure to the therapeutic fluid chamber up to said reference pressure.

6. The device of claim 1, further comprising an output valve adapted to dispense therapeutic fluid from the therapeutic liquid chamber.

7. The device of claim 1, further comprising an input valve adapted to receive therapeutic fluid into the therapeutic liquid chamber.

8. The device of claim 1, wherein said therapeutic fluid chamber and said working pressure chamber further comprises a syringe and syringe piston mechanically attached to said pressure control assembly, wherein said pressure control assembly is inserted into the open end of said syringe, wherein said therapeutic fluid chamber is above the syringe piston and wherein said working pressure chamber is between the syringe piston and said pressure control assembly, and wherein said pressure control assembly maintains a constant pressure within the syringe to support a constant fluid flowrate exiting the syringe.

9. A therapeutic liquid dispensing device comprising:
a first chamber that is provided by a syringe that is filled with therapeutic liquid and adapted to dispense said liquid;
a second chamber adapted to provide a working pressure at or below a reference pressure;
a displaceable piston positioned inside said syringe and separating said first chamber from said second chamber, said second chamber mechanically connected to said first chamber through said displaceable piston;
a third chamber adapted to provide pressurized gas from the third chamber to the second chamber;
a pressure control assembly positioned between said third chamber and said second chamber, said pressure control assembly adapted to regulate the working pressure and provide a constant working pressure inside the second chamber to a reference pressure for the entire duration of liquid dispensation;
a pressure relief apparatus in fluid connection with the second chamber for venting any pressure delivered from the third chamber in excess of the reference pressure;
wherein said second chamber is provided by a syringe that is pressure regulated by the pressure control assembly where the regulated pressure in the second chamber provides the working pressure for displacement of the displaceable piston in the syringe which ejects the therapeutic agent from the first chamber of the syringe; and
a valve component positioned within the pressure control assembly that can be actuated between two states to provide pressure venting of the second chamber of the syringe to atmosphere or provide fluid connection between the second chamber and the pressure control assembly.

* * * * *